US012766243B2

(12) United States Patent
Prasad et al.

(10) Patent No.: US 12,766,243 B2
(45) Date of Patent: Oct. 20, 2026

(54) INTRAVASCULAR CATHETER CARE PRE- AND POST-FLUSHING

(71) Applicant: Becton, Dickinson and Company, Franklin Lakes, NJ (US)

(72) Inventors: Shishir Prasad, Ramsey, NJ (US); Ajinkya Madhukar Joglekar, Edgewater, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 975 days.

(21) Appl. No.: 17/989,306

(22) Filed: Nov. 17, 2022

(65) Prior Publication Data

US 2024/0165320 A1 May 23, 2024

(51) Int. Cl.

*A61M 25/00* (2006.01)
*A61M 5/14* (2006.01)
*A61M 39/16* (2006.01)
*A61M 39/00* (2006.01)

(52) U.S. Cl.

CPC .............. *A61M 5/14* (2013.01); *A61M 25/00* (2013.01); *A61M 39/162* (2013.01); *A61M 2005/1403* (2013.01); *A61M 2025/0019* (2013.01); *A61M 2039/0018* (2013.01)

(58) Field of Classification Search

CPC ..................................................... A61M 39/16
See application file for complete search history.

(56) References Cited

U.S. PATENT DOCUMENTS

| | | | | |
|---|---|---|---|---|
| 8,671,496 | B2 | 3/2014 | Vaillancourt et al. | |
| 8,696,820 | B2 | 4/2014 | Vaillancourt et al. | |
| 11,083,847 | B2 | 8/2021 | Mahmoodian | |
| 11,344,715 | B2 | 5/2022 | Erekovcanski et al. | |
| D965,777 | S | 10/2022 | Marici et al. | |
| 2013/0061414 | A1 | 3/2013 | Swist et al. | |
| 2013/0171030 | A1* | 7/2013 | Ferlic .................... | A61M 39/20 422/294 |
| 2015/0374968 | A1 | 12/2015 | Solomon et al. | |
| 2016/0185514 | A1* | 6/2016 | Tennican ............... | A61B 90/70 220/23.83 |
| 2016/0325089 | A1 | 11/2016 | Burkholz | |
| 2017/0181810 | A1 | 6/2017 | Tennican | |
| 2020/0121858 | A1 | 4/2020 | Anderson et al. | |
| 2021/0008237 | A1 | 1/2021 | Okman et al. | |
| 2021/0008283 | A1 | 1/2021 | San Solo et al. | |

(Continued)

*Primary Examiner* — Kevin Joyner
(74) *Attorney, Agent, or Firm* — Servilla Whitney LLC

(57) ABSTRACT

An intravascular catheter care device comprising a flush syringe having an integrated disinfecting unit associated therewith and a method for disinfecting an intravascular catheter, wherein the disinfecting unit includes a first disinfecting pad enclosed between a first and second layer of a flexible peel film. The first layer can be removed from the second layer to expose the first disinfecting pad. A second disinfecting pad can be enclosed between either the second layer of the peel film and a third layer of the peel film or between a second layer of the peel film and a cap that can be secured to the connector. The second layer can be removed from the third layer or the cap to expose the second disinfecting pad. The first pad can be used to disinfect the connector of the intravascular catheter prior to flushing and the second pad can be used after flushing.

15 Claims, 2 Drawing Sheets

(56) References Cited

U.S. PATENT DOCUMENTS

| | | | |
|---|---|---|---|
| 2021/0187266 | A1 | 6/2021 | Ryan |
| 2022/0233836 | A1 | 7/2022 | Leibowitz |
| 2022/0273881 | A1 | 9/2022 | Mahmoodian et al. |

* cited by examiner

INTRAVASCULAR CATHETER CARE PRE- AND POST-FLUSHING

BACKGROUND OF THE INVENTION

Field of the Invention

The present disclosure relates generally to the care of a catheter device. More particularly, the present disclosure relates to an integrated intravascular catheter cleaning and disinfecting device for use in disinfecting a connector of the catheter pre-flushing and post-flushing of the catheter.

Description of Related Art

Intravascular catheter care and standards of practice usually recommend that flush procedures be performed after catheter placement, before fluid infusion, and before and after drug administration, blood sampling, transfusions, and parenteral nutrition. The goal of these flush procedures is to confirm catheter patency, avoid drug incompatibilities, ensure complete drug dose administration, prevent thrombus formation, and minimize the risk of blood stream infections.

Catheter-related bloodstream infections are common and are caused by bacterial/fungi in patients with intravascular (IV) catheters. These infections can result in significant illness, or even death, as well as, excess medical costs. Current recommended practice is for the medical practitioner to perform a stepwise disinfecting process. This process requires several disinfecting steps, such as pre-flushing and post-flushing, prior to medication push or fluid withdrawal through the catheter port and IV line, which makes intravascular catheter care and IV line maintenance a very burdensome and time consuming process.

Protective caps or syringe collars containing disinfectants and/or antimicrobial agents therein have been designed as a way to reduce these infections. These caps or collars can be associated with an exit port of a flush syringe or with an IV port prior to connection of the flush syringe with the catheter port as a way to reduce infections. However, these additional caps/collars may be difficult to manipulate or attach to the syringe or IV port, resulting in an operator error. Additionally, the use of these caps/collars increases the overall cost of the device due to the increased number of manufactured components, increased packaging costs, and increased storage space due to the larger footprint created by these caps/collars.

An IV connector cleaning device that is integrated with the flush syringe to disinfect the connector, pre-flushing and post-flushing, in a cost-effective manner would be beneficial in reducing infections while decreasing manufacturing and storage costs.

SUMMARY OF THE INVENTION

Accordingly, provided are improved systems, devices, products, apparatus, and/or methods for intravascular catheter care and cleaning in a cost-effective manner having less manufactured components and require less packaging and storage space.

In accordance with an aspect, the present disclosure is directed to an intravascular catheter care device comprising a flush syringe configured for flushing an intravascular catheter and a disinfecting unit associated with the flush syringe. The disinfecting unit can be attached to the flush syringe, making it intuitive for the user to clean the connector before IV access. According to one embodiment, the disinfecting unit can be attached to the distal tip of the flush syringe. According to another embodiment, the disinfecting unit can be attached to the outer wall of the barrel of the flush syringe. The disinfecting units can be attached to the flush syringe by any well-known technique, including, but not limited to, the use of pressure or temperature sensitive adhesive, mechanical attachment, thermoforming or injection molding with one or more frangible portions enabling the removal of the disinfecting unit from the flush syringe, and the like.

In another embodiment, instead of attaching the disinfecting unit to the flush syringe itself, the disinfecting unit can be co-packaged with the flush syringe.

The disinfecting unit comprises at least a first disinfecting pad enclosed within a flexible peel film. The peel film can include a first layer and a second layer, wherein the first layer is configured for removal from the second layer to expose the first disinfecting pad. The first disinfecting pad is removable from the disinfecting unit for one or pre-flush or post-flush cleaning of a connector of the intravascular catheter. The remaining components of the disinfecting unit can be set aside for future use. The first disinfecting pad can have a patterned surface configured for increasing scrubbing and disinfecting efficiency of the pad and can be formed from a woven or a foam material. The first disinfecting pad can be soaked in any well-known disinfecting or antimicrobial material, such as, for example, a 70% aqueous isopropyl alcohol solution.

According to one embodiment, the first disinfecting pad can be used pre-flushing and the disinfecting unit can further comprise a second disinfecting pad configured for cleaning of the connector of the intravascular catheter post-flushing. The second layer of the peel film can separate the first disinfecting pad from the second disinfecting pad and the second layer can be configured for the removal from the first layer to expose the second disinfecting pad. According to one design, the peel film can comprise a third layer and the second disinfecting pad is enclosed between the second layer and the third layer. According to another design, the disinfecting unit can comprise a cap and the second disinfecting pad is located within the cap and the second layer forms a seal with the cap to enclose the second disinfecting pad therein. The cap, including the second disinfecting pad, can be configured to be removably secured onto the connector such that the second disinfecting pad comes into contact with the connector post-flushing. It can be appreciated that the cap can be secured to the connector by any well-known arrangement such as by a threaded engagement, slip fit engagement, and the like.

Similar to the first disinfecting pad, the second disinfecting pad can have a patterned surface to increase its scrubbing and disinfecting efficiency and can be soaked with a well-known disinfecting liquid.

In accordance with another aspect, the present disclosure is directed to an intravascular catheter care device comprising a flush syringe configured for flushing the intravascular catheter and a disinfecting unit associated with the flush syringe. The disinfecting unit can comprise at least a first disinfecting pad enclosed within a flexible peel film. The peel film includes a first layer and a second layer, wherein the first layer is configured for removal from the second layer to expose the first disinfecting pad. The disinfecting unit can further include at least a second disinfecting pad, wherein the second disinfecting pad is enclosed between either the second layer of the peel film and a third layer of the peel film or between a second layer of the peel film and a cap. The second layer is configured for the removal from either the third layer or the cap to expose the second disinfecting pad. The first disinfecting pad is removable from the disinfecting unit to enable a user to disinfect the connector of the intravascular catheter prior to flushing or pre-flushing and the second disinfecting pad is usable for disinfecting the intravascular catheter after flushing or post-flushing.

The first and second disinfecting pads can have a patterned surface configured for increasing the scrubbing and disinfecting efficiency of the pads. According to one embodiment, the first and second disinfecting pads can be soaked in a disinfecting solution. It can be appreciated that any well-known disinfecting or antimicrobial material can be used for soaking the first and second disinfecting pads. One example of a disinfecting material that can be used comprises a 70% aqueous isopropyl alcohol solution.

In the design where the disinfecting unit comprises the third layer of the peel film, the second disinfecting pad is removable from the disinfecting unit and is used to disinfect the connector. In the alternative design where the disinfecting unit comprises the cap, the cap including the second disinfecting pad can be removably secured onto the connector post-flushing such that the second disinfecting pad comes into contact with the connector. It can be appreciated that any well-known connection engagement can be used, such as a threaded or slip-fit engagement, to secure the cap onto the connector.

In accordance with yet another aspect, the present disclosure is directed to a method for disinfecting a connector of an intravascular catheter comprising providing a flush syringe configured for flushing the intravascular catheter, the flush syringe comprising an integrated disinfecting unit comprising at least a first disinfecting pad and a second disinfecting pad, wherein the first disinfecting pad is enclosed within a peel film having a first layer and a second layer and the second disinfecting pad is enclosed within the second layer of the peel film and at least one of a third layer of a peel film and a cap. The method further comprises removing the first layer of the peel film and removing the first disinfecting pad, cleaning and disinfecting a connector with the first disinfecting pad prior to flushing of the intravascular catheter, connecting the flush syringe to the connector and flushing the catheter line, and disconnecting the flush syringe from the connector, removing the second layer of the peel film to expose the second disinfecting pad, and cleaning and disinfecting the connector with the second disinfecting pad after flushing.

In the design where the second disinfecting pad is enclosed within the second layer of the peel film and the third layer, the method comprises removing the second disinfecting pad from the disinfecting unit for cleaning and disinfecting the connector. In the design where the second disinfecting pad is enclosed within the second layer of the peel film and the cap, the method comprises removably securing the cap onto the connector so that the second disinfecting pad comes into contact with the connector.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DESCRIPTION OF THE INVENTION

Figure 2B:
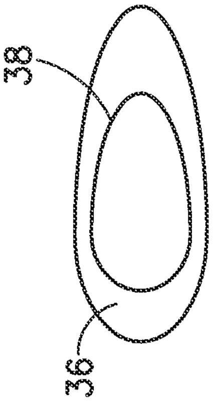
FIG. 2B is a top perspective view of the disinfecting unit of FIG. 2A with the first disinfecting pad removed in accordance with an embodiment of the present invention.

Other than in the operating examples, or where otherwise indicated, all numbers expressing quantities of ingredients, material properties, and so forth used in the specification and claims and Figures are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for contact with a patient and/or engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

Reference is now made to FIGS. 1 and 2A-2D which show an intravascular catheter care device, generally indicated as 10, having an integrated disinfecting unit 12 in accordance with an embodiment of the present invention. The intravascular catheter care device 10 comprises a flush syringe 14 having a distal tip 16 configured for connection to a connector of the intravascular catheter (not shown) for flushing the intravascular catheter. The syringe 14 can be any well-known syringe having a barrel 18 for containing the flushing fluid, such as saline, and having a plunger rod 20 at a proximal end 22 for dispensing the flushing fluid. Although the drawings and description refer to a flushing syringe, it can be appreciated that the disinfecting device of the present disclosure can be integrated with any device that is to be connected to the connector of an intravascular catheter, such as for injecting medication or withdrawing fluid, to ensure proper disinfection of the connector prior to and after use of the device with the intravascular device. The disinfecting unit 12 is associated with the flush syringe, such as being removably secured to the distal tip 16 of the flush syringe 14. It can be appreciated that this disinfecting unit 12 can be secured to the flush syringe 14 by any well-known means, such as with a pressure or temperature sensitive adhesive, mechanical attachment, thermoforming or injection molding with frangible portions, and the like In another embodiment, the disinfecting unit 12 would not be physically attached to the flush syringe 14, but rather co-packaged with the flush syringe 14.

The disinfecting unit 12 includes a first disinfecting pad 30 enclosed within a flexible peel film, generally indicated as 32. The peel film 32 includes a first layer 34 and a second layer 36. The first layer 32 is configured for removal from the second layer 34 to expose the first disinfecting pad 30, as shown in FIG. 2A. The peel film 32 can have a grasping portion 37 for easy removal of the first layer 34 from the second layer 36.

Figure 2D:
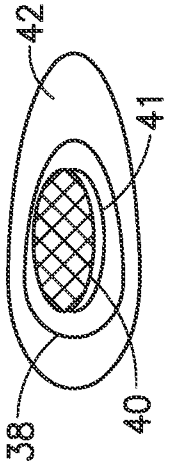
FIG. 2D is a top perspective view of the disinfecting unit of FIG. 2C with the second layer of the peel film removed to show the second disinfecting pad for post-flush connector cleaning in accordance with an embodiment of the present invention.
Figure 2A:
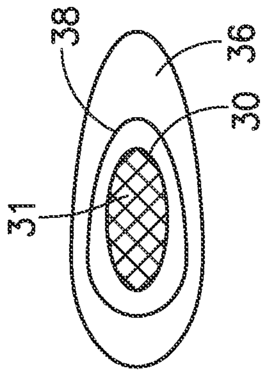
FIG. 2A is a top perspective view of the disinfecting unit of the intravascular catheter care device of FIG. 1 with the first layer of the peel film removed to show the first disinfecting pad for pre-flush connector cleaning in accordance with an embodiment of the present invention.
Figure 2C:
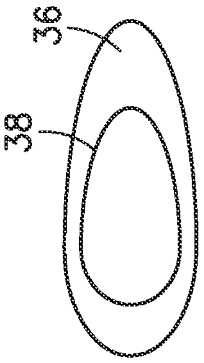
FIG. 2C is a top perspective view of the disinfecting unit of FIG. 2B prior to removal of the second layer of the peel film covering the second disinfecting pad in accordance with an embodiment of the present invention.
Figure 1:
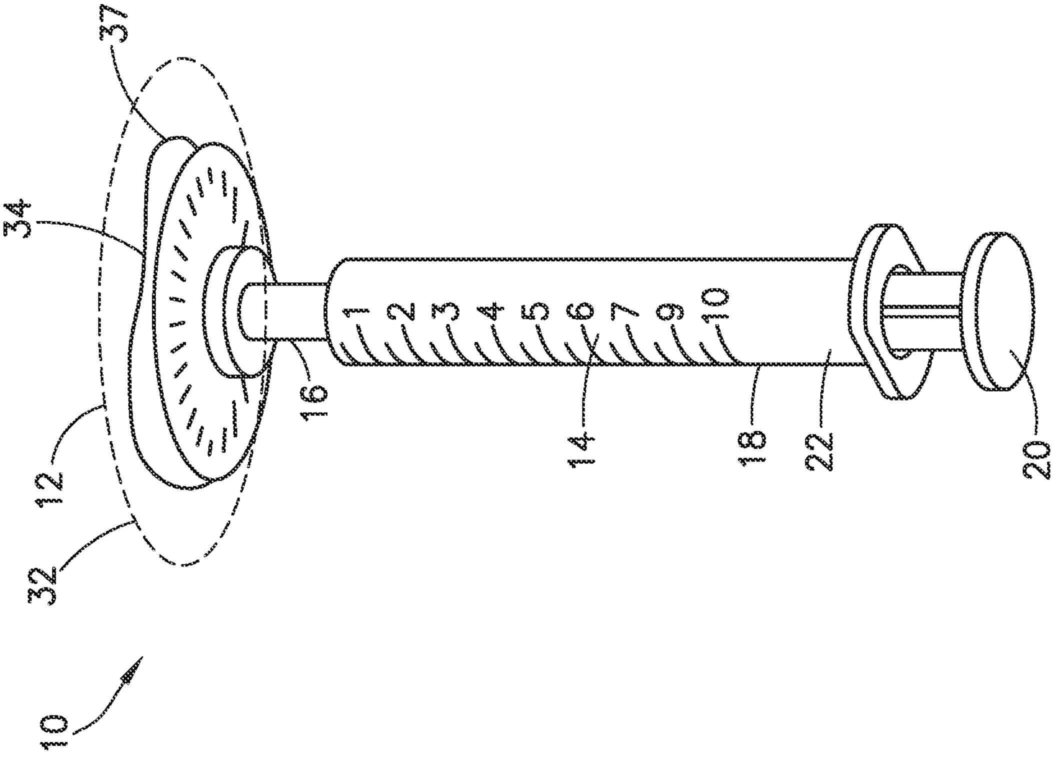
FIG. 1 is side perspective side view of the intravascular catheter care device having an integrated disinfecting unit in accordance with an embodiment of the present invention.

Reference is now made to FIGS. 2B-2D which show a second disinfecting pad 40. The second disinfecting pad is enclosed between the second layer 36 of the peel film 32 and at least one a third layer 42 of the peel film 32. As shown in FIGS. 2A-2D, a seal line 38 secures the second layer 36 to the third layer 42. The second layer 36 is configured for removal from the third layer 42 to expose the second disinfecting pad 40. It can be appreciated that the first disinfecting pad 30 is removable from the disinfecting unit 12 for pre-flush cleaning of the connector of the intravascular catheter and the second disinfecting pad 40 can be removed from the disinfecting unit 12 for post-flush cleaning of the connector of the intravascular catheter.

The first and second disinfecting pads 30, 40 may comprise an antimicrobial composition that is effective in preventing growth and colonization of pathogens, and that is safe for use in an infusion system. An antimicrobial composition in accordance with the present invention generally comprises an antimicrobial or biocidal agent effective against various forms and strains of bacteria which may cause infection within a patient. According to one embodiment, the disinfecting liquid can comprise a 70% aqueous isopropyl alcohol, however, any well-known antimicrobial or biocide disinfecting agent can be used. The first and second disinfecting pads 30, 40 can be made of either non-woven material or foam, made from polymers such as, but not limited to polyurethane, polyethylene, or polystyrene. The first and second disinfecting pads 30, 40 can be patterned, as shown by 31, 41 for better scrubbing efficiency.

Figure 4A:
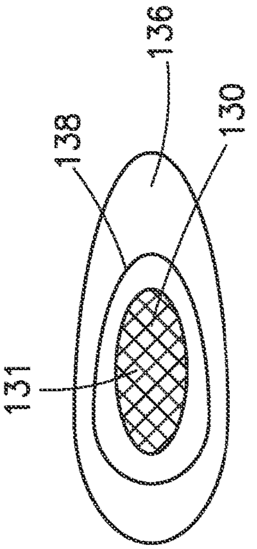
FIG. 4A is a top perspective view of the disinfecting unit of the intravascular catheter care device of FIG. 3 with the first layer of the peel film removed to show the first disinfecting pad for pre-flush connector cleaning in accordance with an embodiment of the present invention.
Figure 4B:
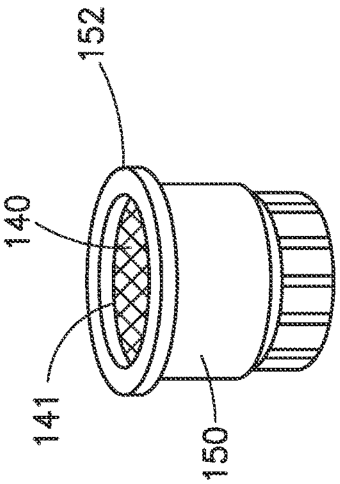
FIG. 4B is a side perspective view of the cap from the disinfecting unit of FIG. 4A, with the first and second peel layers removed to show the second disinfecting pad/cap arrangement for attachment to the connector for post-flush connector cleaning in accordance with an embodiment of the present invention, Corresponding reference characters indicate corresponding parts throughout the several views. The exemplifications set out herein illustrate exemplary embodiments of the disclosure, and such exemplifications are not to be construed as limiting the scope of the disclosure in any manner.
Figure 3:
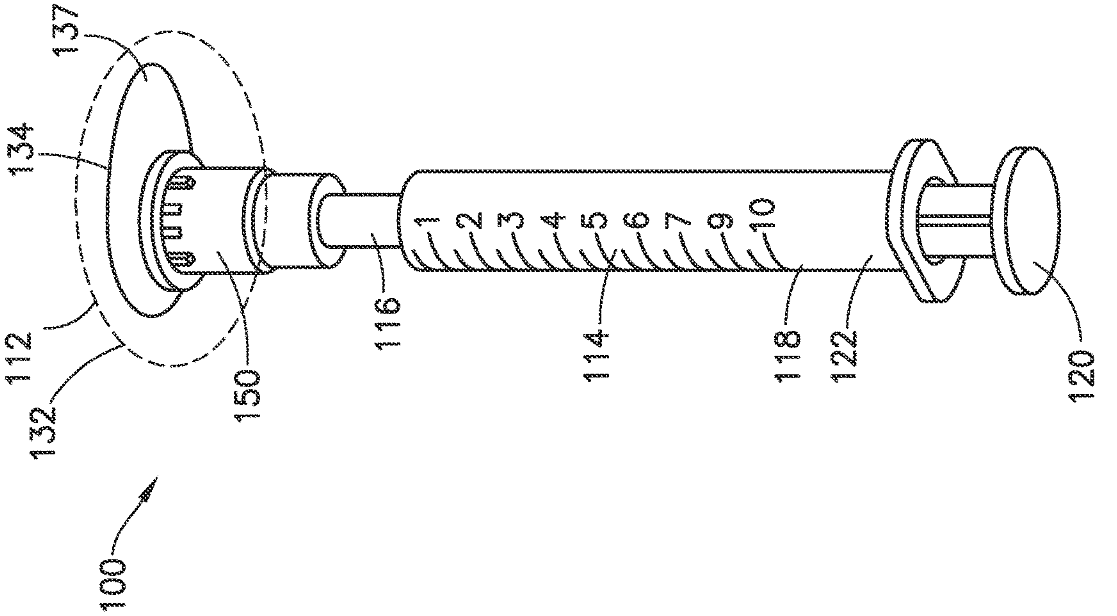
FIG. 3 is side perspective side view of the intravascular catheter care device having an integrated disinfecting unit in accordance with an embodiment of the present invention.

Reference is now made to FIGS. 3 and 4A-4B, which show an intravascular catheter care device, generally indicated as 100, having an integrated disinfecting unit 112 in accordance with another design of the present invention. The intravascular catheter care device 100 comprises a flush syringe 114 having a distal tip 116 configured for connection to a connector of the intravascular catheter (not shown) for flushing the intravascular catheter. The syringe 114 can be any well-known syringe having a barrel 118 for containing the flushing fluid, such as saline, and having a plunger rod 120 at a proximal end 122 for dispensing the flushing fluid. The disinfecting unit 112 is associated with the flush syringe 114, such as being removably secured to the distal tip 116 of the flushing syringe 114. The disinfecting unit 112 includes a first disinfecting pad 130 enclosed within a flexible peel film, generally indicated as 132. The peel film 132 includes a first layer 134 and a second layer 136. The first layer 134 is configured for removal from the second layer 136 to expose the first disinfecting pad 130, as shown in FIG. 4A. The peel film 132 can have a grasping portion 137 for easy removal of the first layer 134 from the second layer 136.

Reference is now made to FIG. 4B which shows a second disinfecting pad 140. A cap 150 is provided for holding the second disinfecting pad 140. The cap 150 is removably secured to the distal tip 116 of the flush syringe 114. The second layer 136 of the peel film 132 is secured to the edges 152 of the cap 150 via a seal line 138. This second layer 136 can be removed from the edges 152 the cap 150 to expose the second disinfecting pad 140. The cap 150 can then be removably secured onto the connector post-flushing such that the second disinfecting pad 140 comes into contact with the connector. It can be appreciated that the cap 150 can be secured to the connector by any well-known engagement, such as by a threaded engagement, a friction fit or slip fit engagement, and the like.

The first and second disinfecting pads 130, 140 may comprise an antimicrobial composition that is effective in preventing growth and colonization of pathogens, and that is safe for use in an infusion system. According to one embodiment, the disinfecting liquid can comprise a 70% aqueous isopropyl alcohol, however, any well-known antimicrobial or biocide disinfecting agent can be used. The first and second disinfecting pads 130, 140 can be made of either non-woven material or foam, made from polymers such as, but not limited to polyurethane, polyethylene, or polystyrene. The first and second disinfecting pads 130, 140 can be patterned, as shown by 131, 141 for better scrubbing efficiency.

The peel film 32, 132, can be formed from any well-known peel film layers, such as, for example, an aluminum peel back layers comprising a plastic sealed aluminum that can be chemically-resistant, light-blocking, non-permeable, and sterile.

Referring back to FIGS. 1, 2A-2D along with FIGS. 3 and FIGS. 4A-4B, the method for disinfecting a connector of an intravascular catheter with the intravascular catheter care device 10, 100 of the invention comprise providing a flush syringe 14, 114 configured for flushing the intravascular catheter with the integrated disinfecting unit 12, 112. The disinfecting unit 12, 112 comprises at least a first disinfecting pad 30, 130 and a second disinfecting pad 40, 140. The first disinfecting pad 30, 130 is enclosed within a peel film 32, 132 having a first layer 34, 134 and a second layer 36, 136. The second disinfecting pad 40, 140 is enclosed within the second layer 36, 136 of the peel film 32, 132 and at least one of a third layer 42 of a peel film 32, 132 or a cap 150. The method further comprises removing the first layer 34, 134 of the peel film 32, 132 and removing the first disinfecting pad 30, 130, cleaning and disinfecting a connector of the intravascular catheter, with the first disinfecting pad 30, 130, prior to or pre-flushing, connecting the flush syringe 14, 114 to the connector and flushing the catheter line, disconnecting the flush syringe 14, 114 from the connector, removing the second layer 36, 136 of the peel film 32, 132 to expose the second disinfecting pad 40, 140, and cleaning and disinfecting the connector with the second disinfecting pad 40, 140 post-flushing. In the FIG. 1 and FIGS. 2A-2D design, the second disinfecting pad 40 is enclosed within the second layer 36 of the peel film 32, 132 and a third layer 42 of the peel film and the method comprises removing the second disinfecting pad 40 from the disinfecting unit 12, 112 for cleaning and disinfecting the connector. In the FIG. 3 and FIGS. 4A-4B design, the second disinfecting pad 140 is placed within cap 150 and sealed by the second layer 136 of the peel film 132. The method comprises removing the second layer 136 to expose the second disinfecting pad 140 and securing the cap 150 onto the connector so that the second disinfecting pad 140 comes into contact with the connector.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. An intravascular catheter care device comprising:

a flush syringe configured for flushing an intravascular catheter; and a disinfecting unit associated with the flush syringe, the disinfecting unit comprising a cap, the cap comprising at least a first disinfecting pad and a second disinfecting pad enclosed within a flexible peel film, the peel film including a first layer and a second layer, wherein the first layer is configured for removal from the second layer to expose the first disinfecting pad and the second layer encloses at least a portion of the second disinfecting pad, wherein the second layer of the peel film separates the first disinfecting pad from the second disinfecting pad, and wherein the second layer is configured for removal from the first layer to expose the first disinfecting pad, and wherein the first disinfecting pad is removable from the disinfecting unit for at least one of pre-flush or post-flush cleaning of a connector of the intravascular catheter.

2. The device of claim 1, wherein the first disinfecting pad has a patterned surface configured for increasing scrubbing and disinfecting efficiency of the first disinfecting pad.

3. The device of claim 1, wherein the first disinfecting pad is used pre-flushing, and wherein the disinfecting unit further comprises the second disinfecting pad configured for post-flush cleaning of the connector of the intravascular catheter.

4. The device of claim 1, wherein the peel film comprises a third layer, and wherein the second disinfecting pad is enclosed between the second layer and the third layer.

5. The device of claim 1, wherein the cap, including the second disinfecting pad, is configured to be removably secured onto the connector post-flushing such that the second disinfecting pad comes into contact with the connector.

6. The device of claim 1, wherein the first disinfecting pad is soaked with a disinfecting liquid.

7. The device of claim 3, wherein the second disinfecting pad has a patterned surface and is soaked with a disinfecting liquid.

8. An intravascular catheter care device comprising:

a flush syringe configured for flushing an intravascular catheter; and a disinfecting unit associated with the flush syringe, the disinfecting unit comprising:

a cap, the cap comprising at least a first disinfecting pad and a second disinfecting pad enclosed within a flexible peel film, the peel film including a first layer and a second layer, wherein the first layer is configured for removal from the second layer to expose the first disinfecting pad and the second layer encloses at least a portion of the second disinfecting pad, wherein the second disinfecting pad is enclosed between the second layer of the peel film and at least one of a third layer of the peel film and the cap, wherein the second layer is configured for removal from at least one of the third layer and the cap to expose the second disinfecting pad, wherein the first disinfecting pad is removable from the disinfecting unit for pre-flush cleaning of a connector of the intravascular catheter and the second disinfecting pad is usable for post-flush cleaning of the connector of the intravascular catheter.

9. The device of claim 8, wherein the first and second disinfecting pads have a patterned surface configured for increasing a scrubbing and disinfecting efficiency of the first and second disinfecting pads.

10. The device of claim 8, wherein the first and second disinfecting pads are soaked in a disinfecting solution.

11. The device of claim 8, wherein the disinfecting unit comprises the third layer of the peel film, and wherein the second disinfecting pad is removable from the disinfecting unit.

12. The device of claim 8, wherein the disinfecting unit comprises the cap, and wherein the cap, including the second disinfecting pad, is configured to be removably secured onto the connector post-flushing such that the second disinfecting pad comes into contact with the connector.

13. A method for disinfecting a connector of an intravascular catheter comprising:

providing the device of claim 8;

removing the first layer of the peel film and removing the first disinfecting pad;

cleaning and disinfecting a connector of the intravascular catheter with the first disinfecting pad prior to flushing;

connecting the flush syringe to the connector and flushing a catheter line;

disconnecting the flush syringe from the connector;

removing the second layer of the peel film to expose the second disinfecting pad; and cleaning and disinfecting the connector with the second disinfecting pad after flushing.

14. The method of claim 13, wherein the second disinfecting pad is enclosed within the second layer of the peel film and a third layer, and wherein the method comprises removing the second disinfecting pad from the disinfecting unit for cleaning and disinfecting the connector.

15. The method of claim 13, wherein the second disinfecting pad is enclosed within the second layer of the peel film and the cap, and wherein the method comprises removably securing the cap onto the connector such that the second disinfecting pad comes into contact with the connector.

* * * * *